US008580086B2

(12) United States Patent
Matsuuchi et al.

(10) Patent No.: US 8,580,086 B2
(45) Date of Patent: Nov. 12, 2013

(54) HIGH CONCENTRATION NO₂ GENERATING SYSTEM AND METHOD FOR GENERATING HIGH CONCENTRATION NO₂ USING THE GENERATING SYSTEM

(71) Applicants: Hidetaka Matsuuchi, Wakayama (JP); Tomoyuki Hirose, Wakayama (JP); Ryuichi Iwasaki, Wakayama (JP); Masaaki Mike, Wakayama (JP); Shigeru Masuda, Wakayama (JP); Hirofumi Hayashi, Wakayama (JP); Toru Tanibata, Wakayama (JP); Joongsoo Kim, Los Altos, CA (US); Sang Hun Lee, San Ramon, CA (US); Jae-Mo Koo, Palo Alto, CA (US); Orion Weihe, Saratoga, CA (US); Andrew Way, San Jose, CA (US)

(72) Inventors: Hidetaka Matsuuchi, Wakayama (JP); Tomoyuki Hirose, Wakayama (JP); Ryuichi Iwasaki, Wakayama (JP); Masaaki Mike, Wakayama (JP); Shigeru Masuda, Wakayama (JP); Hirofumi Hayashi, Wakayama (JP); Toru Tanibata, Wakayama (JP); Joongsoo Kim, Los Altos, CA (US); Sang Hun Lee, San Ramon, CA (US); Jae-Mo Koo, Palo Alto, CA (US); Orion Weihe, Saratoga, CA (US); Andrew Way, San Jose, CA (US)

(73) Assignee: Noxilizer, Inc., Baltimore, MD (US)

( * ) Notice: Subject to any disclaimer, the term of this patent is extended or adjusted under 35 U.S.C. 154(b) by 0 days.

(21) Appl. No.: 13/846,412

(22) Filed: Mar. 18, 2013

(65) Prior Publication Data
US 2013/0220793 A1  Aug. 29, 2013

Related U.S. Application Data

(62) Division of application No. 13/144,928, filed as application No. PCT/US2010/026049 on Mar. 3, 2010, now Pat. No. 8,425,852.

(30) Foreign Application Priority Data

Mar. 3, 2009  (JP) .............................. 2009-049282
Mar. 11, 2009 (JP) .............................. 2009-057925

(51) Int. Cl.
  *C01B 21/36* (2006.01)
(52) U.S. Cl.
  USPC ..................................... 204/157.46; 423/400
(58) Field of Classification Search
  USPC ..................................... 204/157.46; 423/400
  See application file for complete search history.

(56) References Cited

U.S. PATENT DOCUMENTS

| 4,267,027 | A | 5/1981 | Amouroux et al. |
| 6,022,456 | A | 2/2000 | Manning |
| 7,402,289 | B2 | 7/2008 | Tabata |
| 8,057,748 | B2 | 11/2011 | Hooper et al. |
| 2004/0028596 | A1 | 2/2004 | Kleiner |
| 2006/0042155 | A1 | 3/2006 | Nolen |

FOREIGN PATENT DOCUMENTS

| JP | 63-144232A | 6/1988 |
| JP | 08-117558A | 5/1996 |
| WO | 2007/148085 | 12/2007 |

OTHER PUBLICATIONS

Chang et al., "Plasma-assisted removal of NO from Gas streams via ammonia injection," 1997, Environmental Engineering Science, vol. 14, No. 4, pp. 193-200.

*Primary Examiner* — Kishor Mayekar
(74) *Attorney, Agent, or Firm* — Rahman LLC

(57) ABSTRACT

A high concentration $NO_2$ gas generating system including a circulating path configured by connecting a chamber, a plasma generator, and a circulating means, wherein $NO_2$ is generated by circulating a gas mixture including nitrogen and oxygen in the circulating path is provided. The high concentration $NO_2$ gas generating system provides a high concentration $NO_2$ generating system and the high concentration $NO_2$ generating method using the generating system by which $NO_2$ of high concentration (approximately 500 ppm or above) required for a high level of sterilization process in such as sterilization of medical instruments can be simply and selectively obtained. In addition, since indoor air is used as an ingredient, the management of ingredients is simple and highly safe, and the high concentration of $NO_2$ can be simply and selectively prepared on demand.

7 Claims, 13 Drawing Sheets

HIGH CONCENTRATION NO₂ GENERATING SYSTEM AND METHOD FOR GENERATING HIGH CONCENTRATION NO₂ USING THE GENERATING SYSTEM

TECHNICAL FIELD

The present invention relates to a high concentration $NO_2$ generating system and a method for generating high concentration $NO_2$ using the generating system. More particularly, the present invention relates to a high concentration $NO_2$ generating system for obtaining $NO_2$ of high concentration in a simple and selective manner by using the air as an ingredient, and a method for generating a high concentration $NO_2$ using the generating system.

BACKGROUND ART

Conventionally, as sterilizing methods of medical instruments, high-pressure steam sterilization (hereinafter, simply referred to as "AC") and ethylene oxide gas sterilization (hereinafter, simply referred to as "EOG sterilization") have been widely used.

AC is a sterilization method in which an item to be sterilized is exposed under a high temperature at approximately 135° C., and has been widely used for medical instruments made of metal. However, there is a disadvantage that limitations exist in items to be sterilized since sterilization is performed under a high temperature condition. For example, there is a problem that heat labile materials such as plastics cannot be sterilized by AC.

On the other hand, EOG sterilization can be used for plastics since it can be performed at a lower temperature of 70° C. or below. However, due to its toxicity and risk of explosion, there is a disadvantage that EOG needs to be securely stored so as not to cause a problem associated with hygienics and safety, and sufficient care needs to be taken in handling. In addition, when EOG is supplied from a tank (cylinder) to a sterilizing apparatus via a pipe, the occurrence of weight reduction needs to be constantly monitored by measuring the weight of the cylinder for the purpose of preventing unexpected leakage from such as the pipes.

Besides those sterilization methods, a sterilization method using hydrogen peroxide ($H_2O_2$) has been used. As compared with EOG, hydrogen peroxide is simple to use and manage, and is useful from the safety perspective. However, since hydrogen peroxide is used in the form of an aqueous solution, the permeability to detail portions such as an inside of a tube is inferior to the AC or EOG sterilization.

As an alternative method to the AC or EOG sterilization, as shown in Japanese Unexamined Patent Publication No. 240864/1988, a sterilization method using high concentration ozone ($O_3$) has also been used in which high concentration ozone is generated by providing a circulating pump in a position downstream from the ozone tank and upstream from the ozonizer and circulating ozone therethrough. In the method, an advantage exists that the generation of ozone and the decomposition of ozone after use are simple. However, there are disadvantages that high concentration ozone is explosive and gives the substantial damage to plastics.

As a sterilization method with no risk of explosion as compared with the above-mentioned various sterilization methods, a sterilization method using a nitrogen oxide gas (hereinafter, also simply referred to as "NOx") has been proposed. In the method of Japanese Unexamined Patent Publication No. 162276/1983, for example, a gas mixture which is obtained by performing a plasma treatment to the gas mixture of oxygen and nitrogen is used for the purpose of sterilizing *Escherichia coli* present on such as food surface. In the method, a gas mixture of nitrogen oxide and ozone is prepared by performing the plasma treatment to a gas mixture introduced from an oxygen cylinder and nitrogen cylinder. The prepared gas mixture is sprayed on the surface of food to sterilize *Escherichia coli* present on the surface. Since the sterilization process can be performed at a moderate temperature, there are advantages that the method can be used for various items to be sterilized, and that sterilant gas does not need to be stored since nitrogen oxide is generated on demand.

DISCLOSURE OF INVENTION

In the sterilizing apparatus of Japanese Unexamined Patent Publication No. 162276/1983, however, nitrogen oxide is prepared by so called "single pass", a single plasma treatment of a gas mixture of oxygen and nitrogen. In addition, nitrogen oxide is sprayed on the surface of food in an open space and the nitrogen oxide after the treatment is directly released to the atmosphere. As a result, the concentration of sterilant gas including nitrogen oxide is, at most, an order of several ppm and is useful to the extent of sterilizing *Escherichia coli* (and sterilization is performed on *Escherichia coli* present only on the surface of food). Accordingly, there is a problem that the method can never be used for the purpose of a high level of sterilization where enhanced reliability is desired (for example, medical instruments attached with germs; more specifically, sterilization of a microspace such as between scissors and an inside of a tube).

The present invention is provided in view of the above-mentioned problems. By focusing on the fact that nitrogen dioxide (hereinafter, also simply referred to as "$NO_2$") exhibits a high sterilizing effect among other sterilant gases including nitrogen oxide, an object of the present invention is to provide a high concentration $NO_2$ generating system and a method for generating high concentration $NO_2$ using the generating system, by which $NO_2$ of high concentration (approximately 500 ppm or above) required for a high level of sterilization process in such as sterilization of medical instruments can be simply and selectively obtained. Another object of the present invention is to provide a high concentration $NO_2$ generating system and a method for generating high concentration $NO_2$ using the generating system, by which the high concentration of $NO_2$ can be simply and selectively prepared on demand since the management of ingredients is unnecessary due to the use of indoor air as an ingredient.

The high concentration $NO_2$ generating system according to the present invention is shown in FIG. 1.

The system is configured by a chamber, $NO_2$ sensor, flow resistor, flow meter, plasma generator, pressure meter, circulating pump, dry air supply apparatus, and exhaust pump.

Preferably, the circulating means is a pressure device, and the circulating path is configured by connecting the plasma generator to the chamber at a downstream side of the path, connecting the pressure device to the plasma generator at a downstream side of the path, and connecting the chamber to the pressure device at a downstream side of the path.

Preferably, a flow resistive portion is connected between the chamber and the plasma generator.

Preferably, the circulating path further includes an $NO_2$ concentration measuring means.

Preferably, the $NO_2$ concentration measuring means is disposed within the chamber, or between the chamber and the flow resistive portion.

Preferably, the circulating path further includes an inlet portion for introducing the gas mixture, and the inlet portion includes a closure means and a gas drying means.

Preferably, the closure means is closed by detecting an internal pressure in the circulating path which increases by supplying the gas mixture into the circulating path under a reduced pressure.

Preferably, the flow resistive portion is an orifice.

The present invention is a method for generating high concentration $NO_2$, including circulating an NOx gas mixture in a circulating path formed by a chamber, a plasma generator, and a circulating means until $NO_2$ concentration reaches 500 ppm to 100,000 ppm by using the high concentration $NO_2$ gas generating system.

Preferably, ambient air is employed for the gas mixture.

Preferably, dry air with a dew point from 0 to −90° C. is used for the gas mixture.

Preferably, an internal pressure of a plasma generating portion of the plasma generator is from 20 to 90 kPa (absolute pressure).

In the case the safety is a significant concern, preferably, a pressure difference between atmospheric pressure and an internal pressure of an interval from the pressure device through the chamber connected to the pressure device at the downstream side of the path to the flow resistive portion connected to the chamber at the downstream side of the path is set between approximately −1 and −50 kPa (relative pressure).

In the case the compactness of the system is a significant concern, an internal pressure of an interval from the pressure device through the chamber connected to the pressure device at the downstream side of the path to the flow resistive portion connected to the chamber at the downstream side of the path is maintained to be a positive pressure relative to atmospheric pressure.

Preferably, a flow volume of the NOx gas mixture circulating in the circulating path is 5 LPM or above.

BEST MODE FOR CARRYING OUT THE INVENTION

Figure 1:
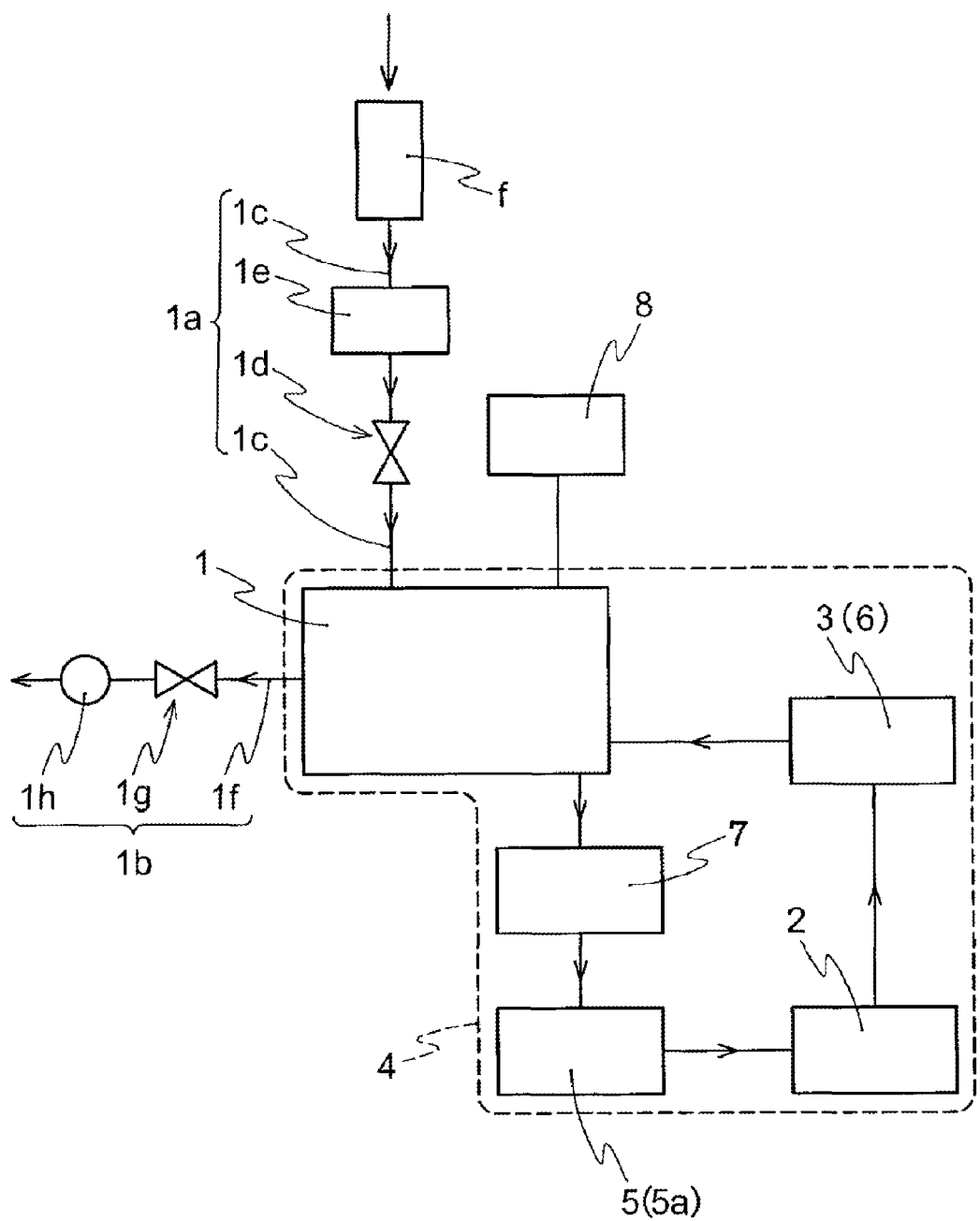
FIG. 1 is an explanatory view illustrating a high concentration $NO_2$ generating system according to an Embodiment of the present invention.

The high concentration $NO_2$ gas generating system according to the present Embodiment includes a circulating path 4 in which a chamber 1, a plasma generator 2, and a circulating apparatus 3 are connected as shown in FIG. 1. More specifically, the circulating path 4 is configured to include the chamber 1, a flow resistive portion 5 connected to the chamber 1 at the downstream side of the path via a pipe, the plasma generator 2 connected to the flow resistive portion 5 at the downstream side of the path via a pipe, and the circulating apparatus 3 connected to the plasma generator 2 at the downstream side of the path via a pipe. The circulating apparatus 3 is further connected to the chamber 1 at the upstream side of the path via a pipe such that a cyclic circulating path 4 is formed by the chamber 1, flow resistive portion 5, plasma generator 2, and circulating apparatus 3. By the operation of the circulating apparatus 3, a gas mixture including nitrogen and oxygen circulates in the circulating path 4 to generate $NO_2$.

The chamber 1 is an airtight compartment for containing a high concentration $NO_2$ gas to be generated. The chamber 1 has a rectangular box shape in the present Embodiment, however, it may have a spherical shape or cylindrical shape. Since the chamber 1 of the present Embodiment forms the circulating path 4, a flow outlet, a flow inlet, and an openable and closable gas supply opening for taking out the high concentration $NO_2$ gas are formed.

The chamber 1 of the present Embodiment includes an inlet portion 1a for introducing the gas mixture therein and a gas supply portion 1b for exhausting the gas in the chamber 1. The inlet portion 1a includes an inlet pipe 1c connected to the inlet opening of the chamber 1, a closure means 1d for opening/closing for an air flow through the inlet pipe 1c, and a gas drying means 1e for drying the gas mixture. The reference numeral f is a filter. The gas drying means 1e dries the gas mixture introduced in the chamber 1 to prevent impurities from attaching to such as the plasma generator 2, and to prevent corrosion of the components such as an electrode and packing by inhibiting nitrification of NOx. In the present Embodiment, an air dryer is employed as the gas drying means 1e.

In the present Embodiment, an air drive valve is used as the closure means 1d. With a pressure detecting means 8 (pressure sensor), the air drive valve detects the pressure in the circulating path 4 which increases by supplying a gas mixture into the circulating path 4 controlled under a reduced pressure. The air drive valve is controlled such that it is electrically driven to close when the differential pressure relative to the ambient air is approximately from −1 to −50 kPa (relative pressure). In addition to this, an air drive valve or an electromagnetic valve which automatically closes at a predetermined internal pressure may be employed as a closure means 1d. Furthermore, the closure means 1d may be configured by a gas drying means 1e including a valve for blocking an air flow at the same time of shutting down operation.

It is noted that the inlet portion 1a for introducing the gas mixture may be provided in the circulating path besides the chamber 1, and may be connected, for example, to the pipe at the upstream side from the plasma generator 2.

The gas mixture is a gas including nitrogen and oxygen which are ingredients for generating high concentration $NO_2$ gas, and the air is employed as the gas mixture in the present Embodiment. In the present Embodiment, a tip of the inlet pipe 1c, therefore, is open for serving as an air inlet opening and includes an air filter. In addition to the air, a gas in which nitrogen and oxygen are composed at a ratio of between 95:5 and 5:95 and which is filled in a cylinder may be employed as a gas mixture. In such a case, the tip of the inlet pipe is connected to the cylinder.

The gas supply portion 1b includes an exhaust pipe 1f, a closure means 1g, and an exhaust pump 1h. By opening/closing the closure means 1g and driving the exhaust pump 1h, the high concentration $NO_2$ gas retained in the chamber 1 including the circulating path 4 as well as impurities and gases such as vapors can be exhausted in an exhausting step described later. In the case of the high concentration $NO_2$ gas, by connecting the gas supply portion 1b to a sterilizing chamber for performing a high level of sterilization of such as medical instruments to exhaust the gas, a sterilization apparatus using the high concentration $NO_2$ gas on demand can be formed.

In the present description, a gas including nitrogen and oxygen which is supplied from the outside to the high concentration $NO_2$ generating system as an ingredient is referred to as a gas mixture, a gas including NOx which is generated by circulating through the plasma generator 2 at least once is referred to as an NOx gas mixture, and a gas which reaches a desired level of $NO_2$ concentration by repeating the above-described circulation is referred to as a high concentration $NO_2$ gas.

The volume of the chamber 1 is preferably around 1 to 300 L, more preferably around 20 to 150 L, and most preferably around 30 to 70 L such that the time required for elevating the concentration of $NO_2$ on demand is not too long. The chamber 1 of the present Embodiment has a volume of 40 L.

The chamber 1 is formed by using such as stainless, nickel-chrome alloy, or unsaturated polyester resin (FRP) which is not likely to be corroded by $NO_2$ or nitric acid, and the chamber is stably supported by securing it on a base (not shown).

In the present Embodiment, the flow resistive portion 5 is formed by an orifice 5a. The orifice 5a is provided in the pipe at the downstream side from the chamber 1, and makes up an orifice fluid meter. In the present Embodiment, therefore, it is advantageous that a flow volume of the gas circulating out of the chamber 1 can be measured. In addition to the orifice 5a, the flow resistive portion 5 may be configured in such a manner that a portion of the pipe at the downstream side from the chamber 1 is configured by a narrow pipe to increase the flow resistivity of that portion.

Figure 2:
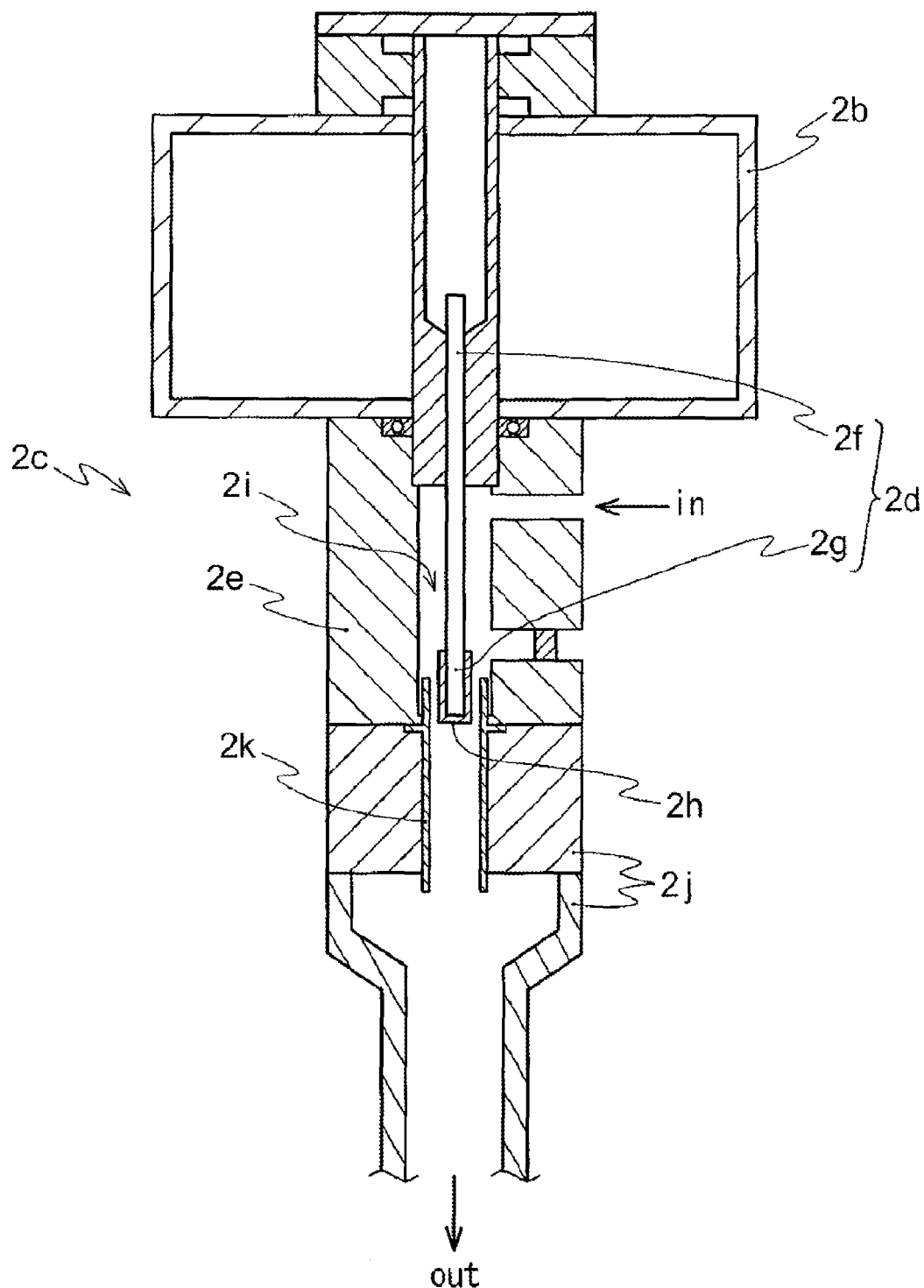
FIG. 2 is an explanatory view illustrating a plasma generating portion in the high concentration $NO_2$ generating system according to an Embodiment of the present invention.
Figure 3:
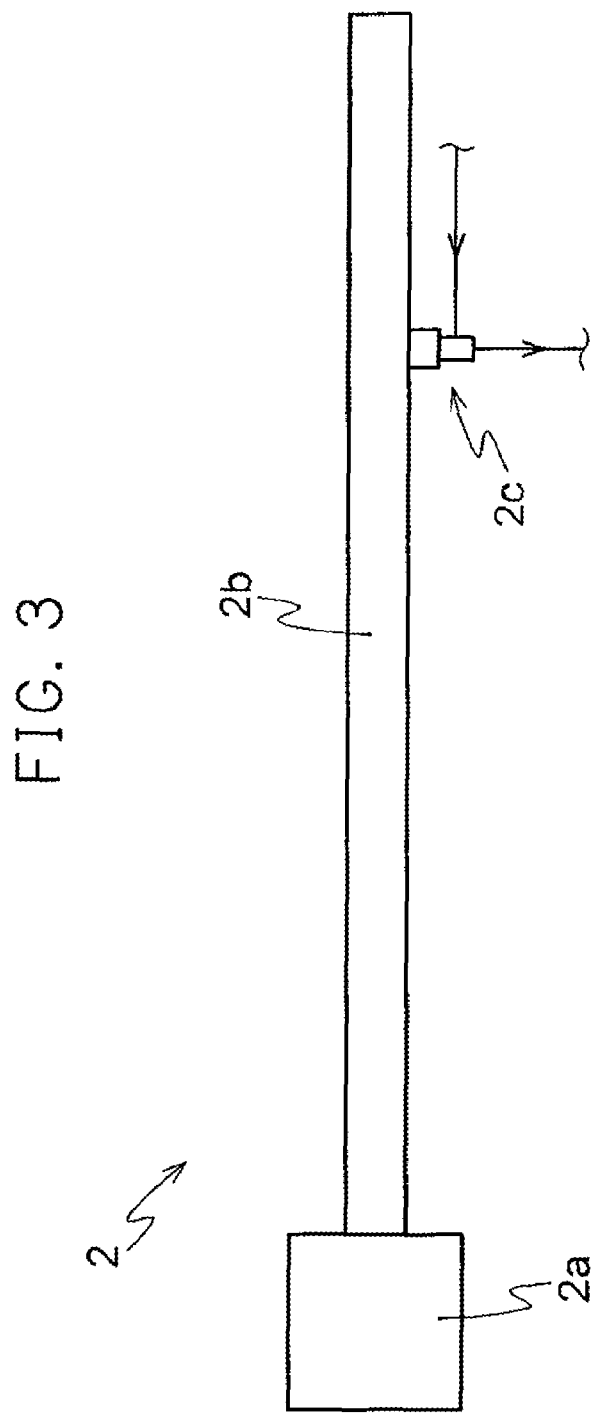
FIG. 3 is an explanatory view illustrating a plasma generator in the high concentration $NO_2$ generating system according to an Embodiment of the present invention.

As shown in FIGS. 2 and 3, the plasma generator 2 is a unit capable of generating a plasma under normal temperature and normal pressure by using microwaves, and is generally configured to include a microwave generating apparatus 2a for generating microwaves with a predetermined wavelength, a waveguide 2b which is connected to the microwave generating apparatus 2a to transmit the microwaves, and a plasma generating portion 2c which is provided integrally with the waveguide 2b.

The microwave generating apparatus 2a generates microwaves at 2.45 GHz, for example, and transmits the microwaves into the waveguide 2b. The microwave generating apparatus 2a, therefore, includes a microwave generating source such as a magnetron for generating microwaves, an amplifier for adjusting the power of the microwaves generated at the microwave generating source to a predetermined power intensity, and a microwave transmitting antenna for emitting the microwaves into the waveguide 2b. As the microwave generating apparatus 2a used in the plasma generator 2, an apparatus of a continuous variable type which is capable of outputting microwave energy of between 1 W and 3 kW, for example, is suitable.

The waveguide 2b is made of a nonmagnetic metal (such as aluminum), for example, has a tubular shape with a rectangular cross section, and transmits the microwaves generated by the microwave generating apparatus 2a toward the plasma generating portion 2c. The waveguide 2b of the present Embodiment is configured by a square tubular assembly using top and bottom plates, and two side plates made of metallic flat plates. In addition to such plate assembly, the waveguide may also be formed by such as extrusion or bending process of a plate member. Moreover, a waveguide 2b with an oval cross section may be used in addition to the waveguide 2b with a rectangular cross section. Furthermore, not only by nonmagnetic metals, but the waveguide may be configured by various members having the waveguide property. The waveguide 2b is grounded in the present Embodiment.

The plasma generating portion 2c is integrally configured with the waveguide 2b, and includes a rod-shaped conducting shaft 2d inserted through the waveguide 2b and a tubular conducting tube 2e. The conducting shaft 2d is further configured by an antenna portion 2f which is inserted into the waveguide 2b to receive the microwaves, and a center electrode 2g protruding externally from the waveguide 2b which, in the present Embodiment, is inserted through the waveguide 2b via an electric insulator. The conducting shaft 2d of the present Embodiment has a circular cross section, however, the conducting shaft with an elliptical, oval, or a long oval cross section may be employed. The conducting shaft 2d of the present Embodiment is formed by using titanium, however, materials capable of conducting microwaves such as titanium alloy, copper, platinum, gold, and silver may be used. A shielding film 2h made of ceramic is formed at a tip of the conducting shaft 2d (center electrode 2g) for preventing arc discharge and protecting the electrode.

In the present Embodiment, the conducting tube 2e has a generally cylindrical shape, and the inner diameter thereof is formed to be larger than the outer diameter of the conducting shaft 2d. The conducting tube is provided to cover the center electrode 2g protruding externally from the waveguide 2b while having the center electrode at the center, and a ring-shaped space 2i is formed between the center electrode 2g and conducting tube 2e. The base end of the conducting tube 2e is electrically conductive and fixed relative to the waveguide 2b, and the conducting tube 2e is thus grounded via waveguide 2b. The conducting tube 2e may have such as a rectangular cross section or an oval cross section in addition to a circular cross section. However, a tip thereof is formed to have a length which terminates with substantially the same position as the tip of the center electrode 2g. It is noted that the conducting tube 2e of the present Embodiment is made using stainless steel, however, it may be made of such as aluminum.

In the conducting tube 2e of the present Embodiment, a ventilation opening is provided at a position toward the base end thereof. By connecting a pipe 2j extending from the flow resistive portion 5 to the ventilation opening, the circulating path 4 connecting from the flow resistive portion 5 to the plasma generator 2 is configured. The gas mixture flowing in the circulating path 4 moves through inside the ring-shaped space 2i toward the end of the center electrode 2g. Furthermore, to an outside edge of the conducting tube 2e, a ceramic shielding tube 2k is inserted to prevent the arc discharge relative to the center electrode 2g. The outside edge of the shielding tube 2k is connected to the pipe 2j directing further toward the downstream of the path to thereby form the circulating path 4.

In the plasma generating portion 2c thus configured, 2.45 GHz of microwave (power is adjustable) generated from the microwave generating apparatus 2a (magnetron) is emitted from the microwave transmitting antenna of the microwave generating apparatus 2a provided at one end of the waveguide 2b to the plasma generating portion 2c. The emitted microwave transmits in the waveguide 2b and is received by the antenna portion 2f of the conducting shaft 2d in the plasma generating portion 2c. The microwave thus received by the antenna portion 2f transmits on the surface of the conducting shaft 2d, and reaches the tip of the center electrode 2g. The tip of the center electrode 2g is electrically coupled to the waveguide 2b, and is disposed nearby the tip of the conducting tube 2e of a ground potential. By the microwaves reached the tip of the center electrode 2g, an intense electric field is formed between the tip of the conducting tube 2e and the tip of the center electrode 2g, especially in the vicinity of the tip of the center electrode 2g. It is noted that the conducting tube 2e is formed to have a resonance point in the 2.45 GHz band, such that an intense electric field is efficiently formed at the tip portion of the center electrode 2g.

By the intense electric field thus formed, partial ionization is generated in nitrogen and oxygen included in the gas mixture supplied via the circulating path 4. As a result, an aggregate of electrons at several tens of thousands degrees in Celsius, ions at substantially normal temperature, neutral atoms at substantially normal temperature, and neutral molecules at substantially normal temperature is composed. Comprehensively, this condition is electrically neutral, and in other words, a plasma state, and more particularly a low-temperature plasma (non-equilibrium plasma) state is formed.

In other words, nitrogen and oxygen of the gas mixture in the vicinity of the end of the center electrode 2g generate dielectric breakdown by being excited through the intense electric field formed by the microwaves, and are displaced from the molecular state to the low-temperature plasma (non-equilibrium plasma) state. The gas under the low-temperature plasma state has a high reactivity with respect to other gases under the low-temperature plasma state or molecular state. Therefore, when the gas mixture including primarily nitrogen and oxygen is introduced to the plasma generating portion 2c, a portion thereof is converted to nitrogen oxides of such as nitrogen monoxide and nitrogen dioxide or to ozone.

$$N_2 + O_2 \rightarrow 2NO \qquad 1.$$

$$N_2 + 2O_2 \rightarrow 2NO_2 \qquad 2.$$

$$3O_2 \rightarrow 2O_3 \qquad 3.$$

It is noted that the conversion ratio is the largest in the case of equation 1. A portion of nitrogen monoxide generated according to equation 1 binds with oxygen under the low-temperature plasma state in the plasma generating portion 2c and is converted to nitrogen dioxide.

$$2NO + O_2 \rightarrow 2NO_2 \qquad 4.$$

The NOx gas mixture including $NO_2$ thus generated circulates through the circulating path 4 or is retained in the chamber 1. During this time, nitrogen monoxide generated according to equation 1 reacts stepwise with oxygen in the NOx gas mixture or with the ozone generated according to equation 3, and is further converted to nitrogen dioxide as shown in equations 5 and 6. As a result, the $NO_2$ concentration increases.

$$2NO + O_2 \rightarrow 2NO_2 \qquad 5.$$

$$NO + O_3 \rightarrow NO_2 + O_2 \qquad 6.$$

Ozone generated according to equation 3 reacts with nitrogen in the NOx gas mixture to generate nitrogen monoxide.

$$N_2 + 2O_3 \rightarrow 2NO + 2O_2 \qquad 7.$$

This nitrogen monoxide is also converted to nitrogen dioxide by the reactions according to equations 5 and 6.

In this manner, when the NOx gas mixture repeats to circulate in the circulating path, the concentration of nitrogen dioxide gradually increases and the high concentration $NO_2$ gas with a desired level of $NO_2$ concentration is obtained. However, when the generated nitrogen monoxide or nitrogen dioxide again passes through the plasma generator 2, a phenomenon occurs that a portion thereof again becomes under the low-temperature plasma state by a dissociation reaction and thus returns to nitrogen or oxygen. Accordingly, when the concentration of the NOx gas mixture reaches a certain level of the high concentration $NO_2$ gas by repeating the circulation, the generation of nitrogen oxide and the dissociation of nitrogen oxide fall under an equilibrium state, so that the enhancement does not proceed further at a certain concentration.

In the high concentration $NO_2$ gas generating system of the present Embodiment, a circulating path 4 including a single plasma generator 2 is illustrated as shown in FIG. 1. However, two or three or more plasma generators 2 may be connected in parallel to form the circulating path 4. This is preferable since the high concentration $NO_2$ gas can be generated in a short time in such case. Furthermore, the circulating path 4 may be divaricated in the plasma generator 2 to provide a plasma generating portion 2c for each of the diverged paths.

The circulating apparatus 3 is configured by using a pressure device 6 in the present Embodiment. A fan may also be used as the circulating apparatus 3. As the pressure device 6, an air pump may be preferably employed, and an air blower or air compressor may also be used. As for the air pump, a diaphragm pump with approximately 20 to 100 watt power and made of fluorine rubber, a plunger pump made of ceramic, or bellows pump may be employed. The pressure device 6 is provided in the pipe for connecting the plasma generator 2 and the chamber 1, and is connected to apply pressure to the chamber 1 side at the downstream side of the path.

As mentioned above, the high concentration $NO_2$ gas generating system of the present Embodiment makes up the cyclic circulating path 4 by connecting the chamber 1, flow resistive portion 5, plasma generator 2, and pressure device 6 in circular via the pipes. By the operation of the pressure device 6, the air (gas mixture) introduced from the inlet portion 1a flows through the circulating path 4, and the NOx gas mixture is generated which includes nitrogen monoxide and nitrogen dioxide generated by the reaction of nitrogen and oxygen displaced to the low-temperature plasma (non-equilibrium plasma) state when passing through the plasma generator 2. The nitrogen monoxide is converted to nitrogen dioxide when it reacts with oxygen in the NOx gas mixture and ozone stepwise. The high concentration $NO_2$ gas can thus be generated by the gradual increase in the concentration of the nitrogen dioxide.

In the high concentration $NO_2$ gas generating system of the present Embodiment, when the NOx gas mixture (including gas mixture) circulates in the circulating path 4 by the operation of the pressure device 6, the gas pressure increases by the pressure device 6. The gas pressure of the NOx gas mixture gradually decreases in the course of the movement of the gas mixture through the circulating path 4 by the resistance of the flow resistive portion 5 as well as the resistance of each path including the resistance in the pipes, and the gas mixture returns to the pressure device 6. As a result, the gas pressures are different in respective regions within the path to create a pressure gradient. Particularly, in the high concentration $NO_2$ gas generating system, the plasma generator 2 is connected to the flow resistive portion 5 at the downstream side of the path, and further the pressure device 6 for increasing the pressure at the chamber side is connected downstream thereto. The system is configured such that the pressure decreases at the flow resistive portion 5, and the internal pressure of the plasma generator 2 at the downstream side of the path is the lowest in the circulating path 4. The gas pressure of the NOx gas mixture moving nearby the center electrode $2g$ of the plasma generating portion $2c$ is thus maintained at a low pressure. Accordingly, even if the nitrogen and oxygen in the NOx gas mixture decrease by continuing the gas circulation, the generation of plasma is stably maintained.

According to the present Embodiment, an $NO_2$ concentration measuring means 7 is further provided in the circulating path 4. The $NO_2$ concentration measuring means 7 employs a sensor which measures a concentration by projecting blue light on a transparent light guiding tube, which is provided at the chamber 1 and is filled with the NOx gas mixture by communicating therewith, to measure the intensity of the transmitting light attenuated in accordance with the concentration of the NOx gas mixture contained in the light guiding tube by means of a light receiving portion. In addition to this, as the $NO_2$ concentration measuring means 7, a sensor or the like may be used which uses the single-wavelength laser induced fluorescence or which detects $NO_2$ by coloring a detecting element utilizing a coupling reaction and measuring the color intensity of the detecting element.

According to the present Embodiment, the $NO_2$ concentration measuring means 7 is connected to the chamber 1 to measure the $NO_2$ concentration of the NOx retained in the chamber 1. As mentioned above, the pressure of the NOx gas mixture flowing through the circulating path 4 generates differences in respective regions. In addition, since the temperature of the NOx gas mixture in the plasma generating portion $2c$ increases, there is a temperature gradient over the circulating path 4. Accordingly, when the $NO_2$ concentration is measured, the correction of the concentration needs to be performed due to the pressure and temperature differences at different measurement positions. However, in the case of measuring the $NO_2$ concentration of the NOx gas mixture retained in the chamber 1 containing the high concentration $NO_2$ gas generated according to the present Embodiment, an accurate measurement can advantageously be performed without needing the correction of the concentration from the perspective of such pressure and temperature. It is noted that, in addition to providing in the chamber 1, the $NO_2$ concentration measuring means 7 is preferably provided between the chamber 1 and the flow resistive portion 5 located at the downstream of the path from the chamber from the same reason.

Hereinafter, an Embodiment of the method for generating the high concentration $NO_2$ gas is described. The method for generating the high concentration $NO_2$ gas according to the present Embodiment is performed by using the above-described high concentration $NO_2$ gas generating system, and is characterized in that the NOx gas mixture is circulated in the circulating path 4 formed by the chamber 1, flow resistive portion 5, plasma generator 2, and pressure device 6 until the $NO_2$ concentration reaches 500 ppm to 100,000 ppm. More specifically, the method includes:

(1) exhausting (vacuuming) the air in the circulating path 4 including the chamber (exhausting step),
(2) filling the dry gas mixture (dry air) in the circulating path 4 including the chamber (air charging step),
(3) starting the plasma generator 2 to generate the NOx gas mixture including $NO_2$ from nitrogen and oxygen in the dry air being displaced to the low-temperature plasma (non-equilibrium plasma) state (starting step),
(4) generating the high concentration $NO_2$ gas by circulating the NOx gas mixture until the $NO_2$ concentration reaches 500 ppm to 100,000 ppm (circulating step), and
(5) supplying the high concentration $NO_2$ gas externally from the chamber 1 (supplying step).

In the exhausting step, the gas remaining in the circulating path 4 including the chamber 1 is released externally by using an exhaust pump $1b$ to obtain a substantially vacuumed state within the circulating path 4. By the step, impurities, moisture and the like remaining in the circulating path 4 are discharged.

Subsequently in the air charging step, the closure means $1d$ of the inlet pipe $1c$ is opened to introduce the external fresh air (gas mixture) into the chamber 1. In the present Embodiment, the ambient air in the installation space of the high concentration $NO_2$ gas generating system is used as the gas mixture. Since the control and operation of a gas cylinder filled with the gas mixture is unnecessary, it is excellent in the perspective of workability and cost, and is preferable in generating the high concentration $NO_2$ gas on demand.

At this time, for the purpose of preventing the attachment of impurities to such as the plasma generator 2 and of inhibiting nitrification of the NOx gas mixture, the dew point of the gas mixture is dried to be, for example, from 0 to $-90°$ C., preferably from $-30$ to $-60°$ C., and $-60°$ C. in the present Embodiment by using the gas drying means $1e$ provided in the air inlet pipe $1c$. In the case the dew point is higher than $0°$ C., attachment of impurities to such as the plasma generator 2 is excessive due to the moisture in the gas mixture, and $NO_2$ decreases since the nitrification of the NOx gas mixture proceeds. On the other hand, in the case the dew point is lower than $-90°$ C., time and cost for drying the gas mixture by using the gas drying means $1e$ increase. Here, the relationship between the dew point and absolute humidity is described. Since one molecule of $H_2O$ reacts with $NO_2$ to generate $HNO_3$, 2.556 mg of $NO_2$ is converted to nitric acid by the presence of 1 mg of $H_2O$. In the case the dew point is $0°$ C., since the absolute humidity is 4.46 mg (mg/L), 11.39 (mg/L) of $NO_2$ is converted to nitric acid. On the other hand, in the case the dew point is $-30°$ C., since the absolute humidity is 0.28 mg (mg/L), 0.71 (mg/L) of $NO_2$ is converted to nitric acid such that the effect of moisture can be made to be 1% or less. In the same manner, 0.24 (mg/L) of $NO_2$ is converted to nitric acid in the case the dew point is $-40°$ C., and 0.00018 (mg/L) of $NO_2$ is converted to nitric acid in the case the dew point is $-90°$ C. In other words, the lower the dew point is, the lower the amount of nitric acid to be converted, resulting in the effective use of the generated high concentration $NO_2$ gas. However, as mentioned above, from the perspective of the increasing time and cost for drying by using the gas drying means $1e$, the dew point is preferably between $-30$ and $-60°$ C.

In the air charging step, by introducing the air into the circulating path 4 under a substantially vacuumed state, the pressure in the circulating path 4 including the inside of the chamber 1 increases. At the time when the differential pressure between the increasing internal pressure and the external pressure is between −1 and −50 kPa (relative pressure), the air drive valve provided as the closure means 1*d* is closed to stop the air supply. In this manner, a "negative pressure state prior to start up" in which the internal pressure of the circulating path 4 is lower than the external pressure is created.

Subsequently in the circulating step, the microwave generating apparatus 2*a* of the plasma generator 2 and the pressure device 6 are started. By way of this, the gas mixture circulates in the circulating path 4, and nitrogen oxide of such as nitrogen monoxide and nitrogen dioxide, and ozone are generated to create the NOx gas mixture by the displacement of nitrogen and oxygen of the gas mixture into the low-temperature plasma state at the plasma generating portion 2*c* of the plasma generator 2. By further circulating the NOx gas mixture, the $NO_2$ concentration is gradually increased in the above-described manner. The circulation of the NOx gas mixture is continued until the concentration of $NO_2$ reaches, for example, approximately 500 to 100,000 ppm, preferably 20,000 to 60,000 ppm, and 40,000 ppm in the present Embodiment to generate the high concentration $NO_2$ gas. In the case the $NO_2$ concentration of the high concentration $NO_2$ gas is less than 500 ppm, the sterilization effect may not be sufficient for a microspace of an item to be sterilized such as an inside of a tube. On the other hand, in the case the concentration is above 100,000 ppm, the sterilization effect is not further increased and the exhausting process of the high concentration $NO_2$ gas becomes troublesome, and the time and cost for generating the high concentration $NO_2$ gas substantially increase.

When the pressure device 6 is actuated and the gas mixture or the NOx gas mixture circulates in the circulating path 4, the internal pressure of the path creates the pressure gradient in which the pressure is the highest at the downstream side of the path from the pressure device 6 and gradually decreases toward the downstream of the path due to the resistance in the flow resistive portion 5, the resistance in the plasma generating portion 2*c*, the resistance in the pipes and the like. Since the circulation is initiated from the above-described negative pressure state prior to start up, the pressure gradient is created by setting the negative pressure prior to start up as the mean value. Furthermore, in the present Embodiment, the negative pressure prior to start up is set by adjusting the timing for operating the closure means 1*d* such that the pressure at the downstream from the pressure device 6 with the highest internal pressure is still lower than the atmospheric pressure. More specifically, the pressure difference between the atmospheric pressure and the gas mixture or the NOx gas mixture present in the interval from the pressure device 6 through the chamber 1 connected to the pressure device 6 at the downstream side therefrom to the flow resistive portion 5 connected to the chamber 1 at the downstream side therefrom is set, for example, between approximately −1 and −50 kPa (relative pressure), preferably −5 and −40 kPa (relative pressure), and −5 kPa (relative pressure) in the present Embodiment. In the case the differential pressure is less than −1 kPa (relative pressure), this may lead to leakage of the NOx gas through the connecting portions of the circulating path, air inlet portion 1*a* for introducing the gas mixture, or the gas supply opening for taking out the high concentration $NO_2$. On the other hand, in the case the differential pressure is above −50 kPa (relative pressure), it is excessive for the purpose of preventing the gas leakage, and the amount of $NO_2$ in the high concentration $NO_2$ gas is likely to decrease. Here, the internal pressure of the chamber 1 and the volume allowed for storing the high concentration $NO_2$ gas are described. In the case the volume of the chamber 1 is 40 L and the atmospheric pressure is 101.3 kPa (absolute pressure), the volume allowed for storing the high concentration $NO_2$ gas is 40 L when the internal pressure of the chamber 1 is 0 kPa (relative pressure). The volume allowed for storing the high concentration $NO_2$ gas is larger when the internal pressure is positive. However, this is not preferable since the high concentration $NO_2$ gas stored in the chamber may leak as described above. On the other hand, the volume allowed for storing the high concentration $NO_2$ gas is 36.1 L when the internal pressure of the chamber 1 is −10 kPa (relative pressure). The volume allowed for storing the high concentration $NO_2$ gas is 28.2 L when the internal pressure of the chamber 1 is −30 kPa (relative pressure), and 20.3 L when the pressure is −50 kPa (relative pressure). In other words, the lower the internal pressure in the chamber 1, the smaller the volume allowed for storing the high concentration $NO_2$ gas. Therefore, the internal pressure of the chamber 1 is preferably negative, and the pressure from −1 to −50 kPa (relative pressure) is more preferable. The lower limit is −50 kPa (relative pressure) from the perspective of the decreasing volume allowed for storing the high concentration $NO_2$ gas, however, there is no problem from the safety perspective when the pressure is lower than that value. With respect to the internal pressure of the circulating path 4, provided that leakage of gas is prevented by a suitable leakage prevention means, the internal pressure of the interval from the pressure device 6 through the chamber 1 to the flow resistive portion 5 may set to be a positive pressure relative to the atmospheric pressure by delaying the timing for operating the closure means 1*d*. Under a high pressure, the amount of $NO_2$ in the high concentration $NO_2$ gas increases at the same level of concentration. This is preferable in that a large amount of $NO_2$ can be generated while using a small chamber 1.

By adjusting the timing for operating the closure means 1*d* or adjusting the value of resistance of the flow resistive portion 5, the pressure inside the plasma generating portion 2*c* of the plasma generator 2 is preferably set between approximately 20 and 90 kPa (absolute pressure), more preferably 40 and 80 kPa (absolute pressure), and 70 kPa (absolute pressure) in the present Embodiment. The dielectric breakdown due to the microwaves for generating a plasma is intensified with a lower gas pressure. Under the small negative pressure of above 90 kPa (absolute pressure), the stability for generating a plasma due to the dielectric breakdown decreases. Particularly, at the stage when the circulation of the NOx gas mixture proceeds and the nitrogen and oxygen contents are decreased, the generation of plasma may stop. On the other hand, in the case of a low pressure of less than 20 kPa (absolute pressure), the dielectric breakdown is accelerated. However, the amount of oxygen and nitrogen in the gas mixture or NOx gas mixture is likely to decrease.

The flow volume of the NOx gas mixture circulating in the circulating path 4 is preferably 5 LPM or more. With a small flow volume of less than 5 LPM, the gas flow rate flowing in the ring-shaped space 2*i* between the center electrode 2*g* of the plasma generator 2 and the conducting tube 2*e* decreases. This may lead to damage the center electrode 2*g* in a short time period, since the cooling effect for the warming center electrode 2*g* is not sufficient. On the other hand, there is no significant problem associated with an increased flow volume. However, this places undue load on the pressure device 6 and increases the operating costs. In view of this, it is preferable when the upper limit is set to be approximately 200 LPM.

In the circulating step, when the concentration of $NO_2$ increases, and at the time when the high concentration $NO_2$ gas ($NO_2$ concentration of 40,000 ppm in the present Embodiment) is reached as a result of the measurement taken by the $NO_2$ concentration measuring means 7, the operation of the plasma generator 2 and pressure device 6 is stopped. In the subsequent supplying step, the high concentration $NO_2$ gas filled in the chamber 1 is supplied from the gas supply opening to a sterilizing chamber 1 for containing such as medical instruments for sterilization in the present Embodiment. It is noted that the gas is supplied through the suction of the vacuumed sterilizing chamber 1 in the present Embodiment, however the gas may be supplied by using a pump.

EXAMPLE

Hereinafter, the high concentration $NO_2$ generating system of the present invention is described in detail by Examples. However, the present invention is not limited to those Examples.

Generation Speed of $NO_2$ in the Case of Changing the Number of Electrodes (Conducting Shaft 2d)

Example 1

Figure 4:
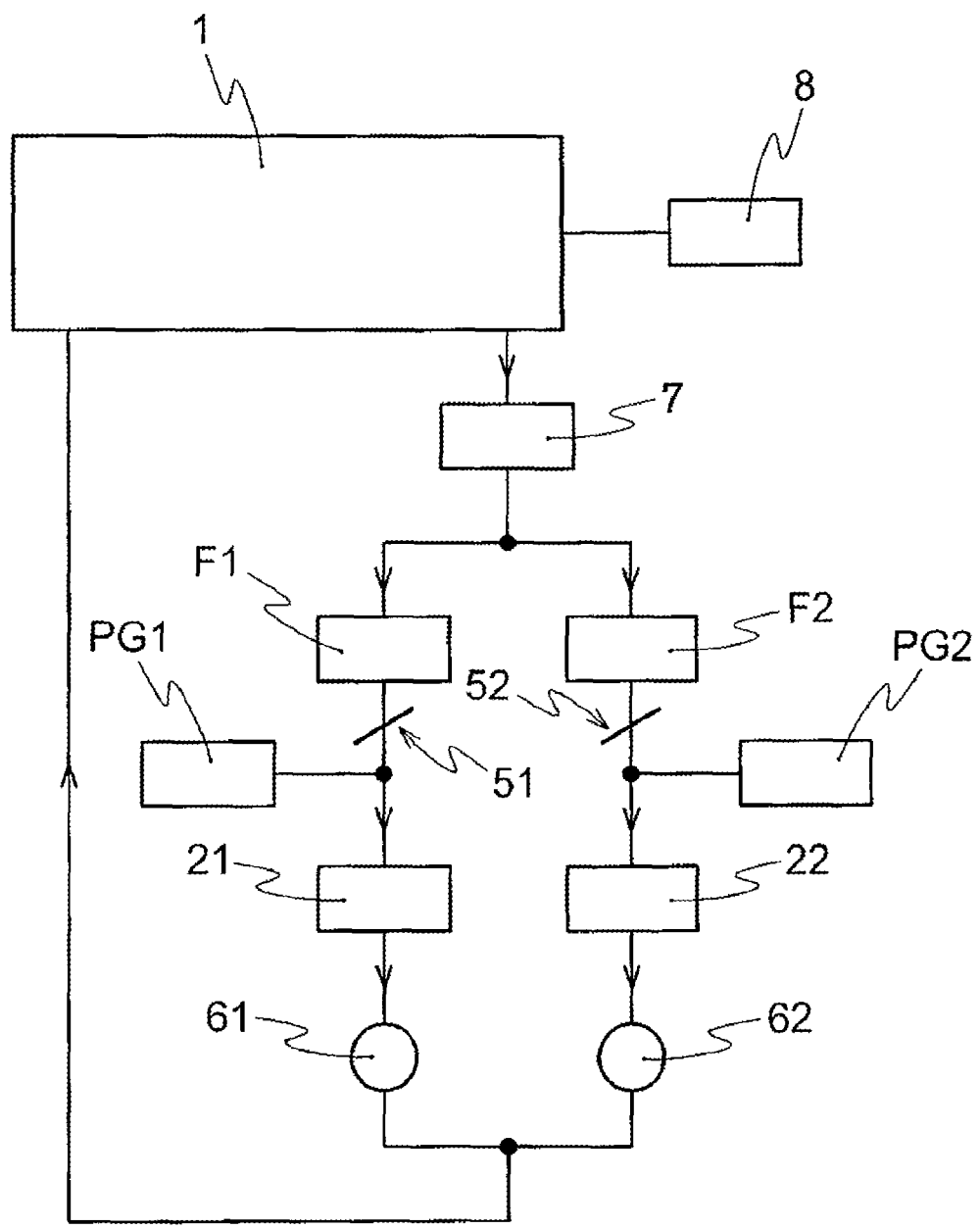
FIG. 4 is an explanatory view illustrating a circulating path used in an Embodiment (Examples 1 to 3 and Comparative Example 4) of the present invention.
Figure 5:
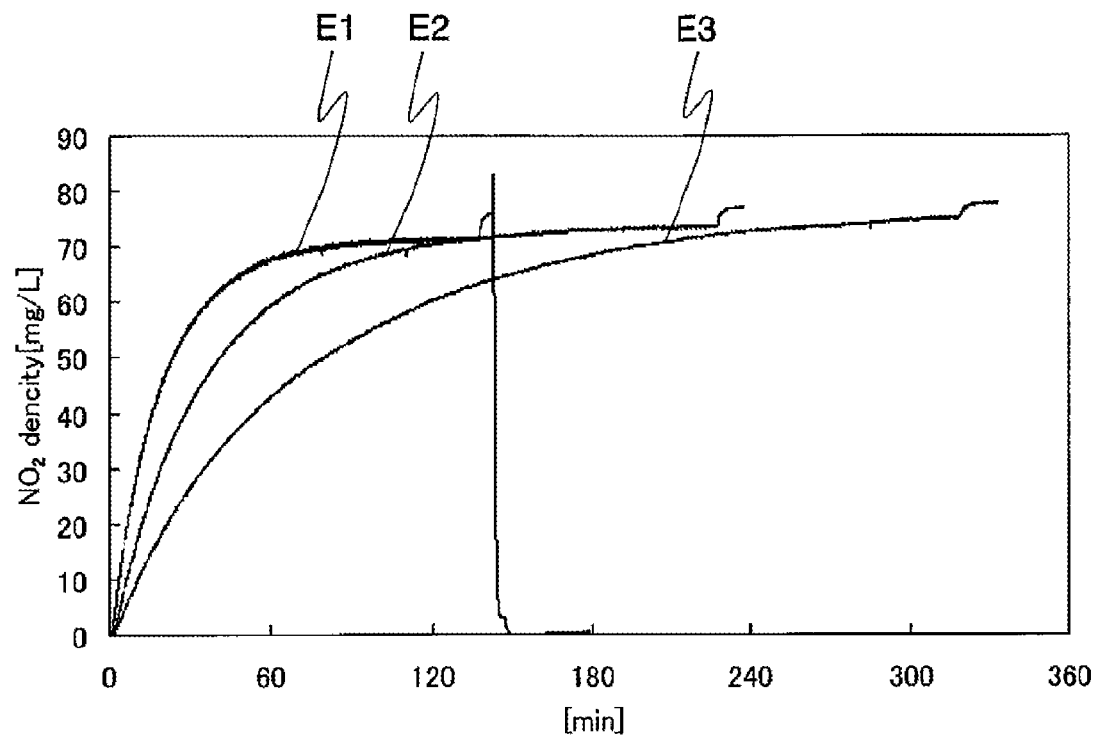
FIG. 5 is a graph illustrating the results of Examples 1 to 3.

In the circulating path shown in FIG. 4, when the internal pressure of the chamber 1 was vacuum (−101 kPa (relative pressure)), the air (dew point −60° C.) was filled such that the internal pressure of the chamber 1 was to be −5 kPa (relative pressure). The air was made to circulate by a pressure device 61 and pressure device 62, and a flow resistive portion 51 and flow resistive portion 52 were adjusted such that the flow meter F1 and flow meter F2 indicated 16 LPM. The pressure in the circulating path at this time was monitored to be from 60 to 70 kPa (absolute pressure) with a pressure meter PG1 and pressure meter PG2. With a plasma generator 21 and plasma generator 22, two electrodes were inserted in the waveguide 2b to apply 160 W of electric power to the plasma generator 21 and plasma generator 22. The concentration of the high concentration $NO_2$ gas was measured over time by the $NO_2$ concentration measuring means 7. The result is shown in FIG. 5. The reference numeral E1 is a graph showing the changes of the concentration of the high concentration $NO_2$ gas over time according to Example 1.

Example 2

Two electrodes were inserted in the plasma generator 21 to apply 160 W of electric power. Electric power was not applied to the other plasma generator 22. Other arrangement was the same as that of Example 1, and the concentration of the high concentration $NO_2$ gas was measured over time. The result is shown in FIG. 5. The reference numeral E2 is a graph showing the changes of the concentration of the high concentration $NO_2$ gas over time according to Example 2.

Example 3

One electrode was inserted in the plasma generator 21 to apply 80 W of electric power. Electric power was not applied to the other plasma generator 22. Other arrangement was the same as that of Example 1, and the concentration of the high concentration $NO_2$ gas was measured over time. The result is shown in FIG. 5. The reference numeral E3 is a graph showing the changes of the concentration of the high concentration $NO_2$ gas over time according to Example 3.

From Examples 1 to 3, it was found that the increase in the concentration of the high concentration $NO_2$ is faster when the number of the electrodes (conducting shaft 2d) is increased. The concentration reached 70 mg/L in approximately 60 minutes in Example 1, the concentration reached 70 mg/L in approximately 120 minutes in Example 2, and the concentration reached 70 mg/L in approximately 240 minutes in Example 3. Therefore, it was found that the number of electrodes (conducting shaft 2d) is proportional to the generating speed of the high concentration $NO_2$ gas.

Here, the concentration of $NO_2$ gas generated in Examples 1 to 3 was approximately 70 mg/L, and it is 36,500 ppm when the unit is converted to ppm. In addition, since $NO_2$ and $N_2O_4$ are present under an equilibrium state in the high concentration $NO_2$ gas, 63,600 ppm of $NO_2$ is theoretically present in practical.

(Generation Speed of $NO_2$ in the Case of Changing the Flow Volume of NOx Gas Mixture Circulating in the Circulating Path)

Example 4

Figure 6:
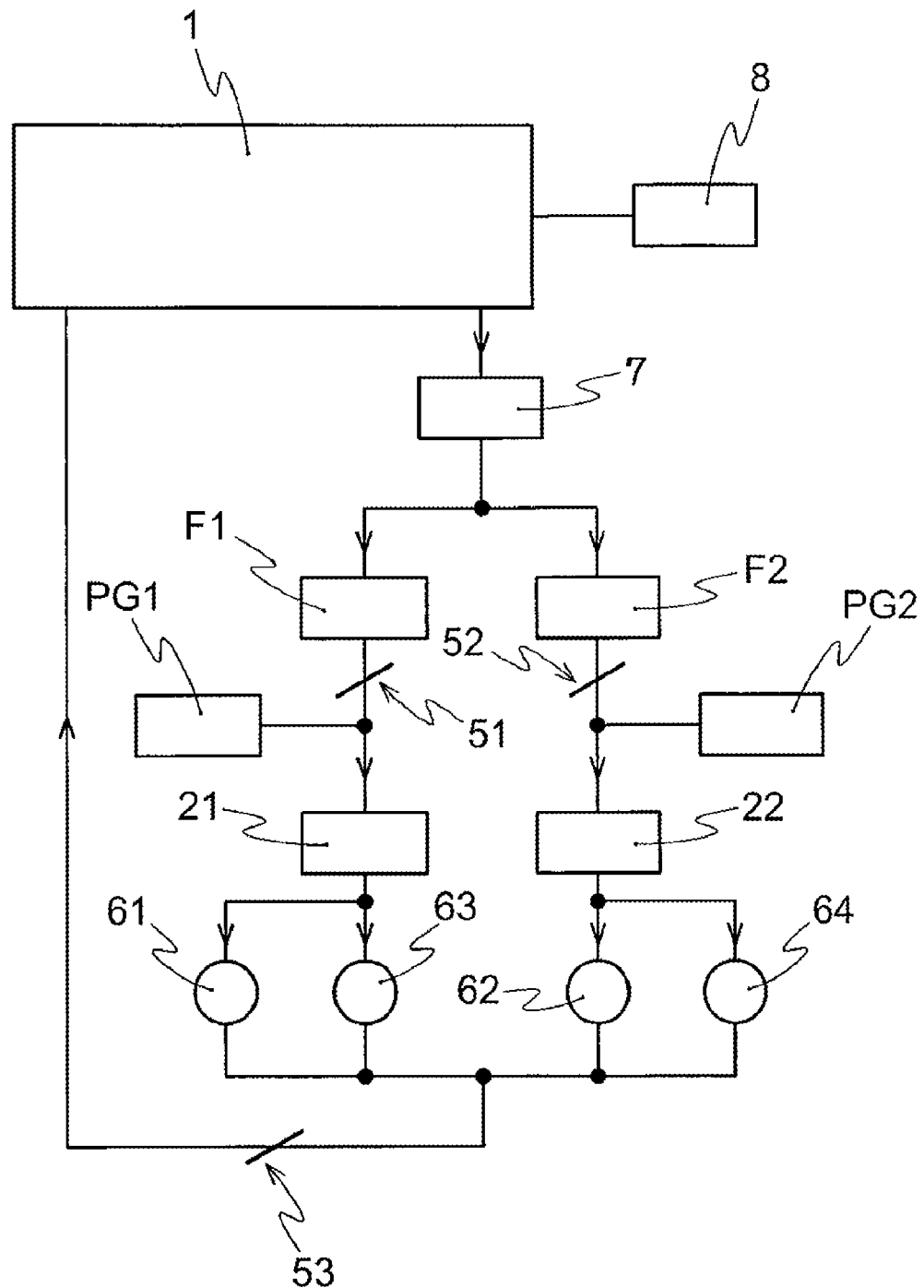
FIG. 6 is an explanatory view illustrating a circulating path used in an Embodiment (Examples 4 to 6) of the present invention.
Figure 7:
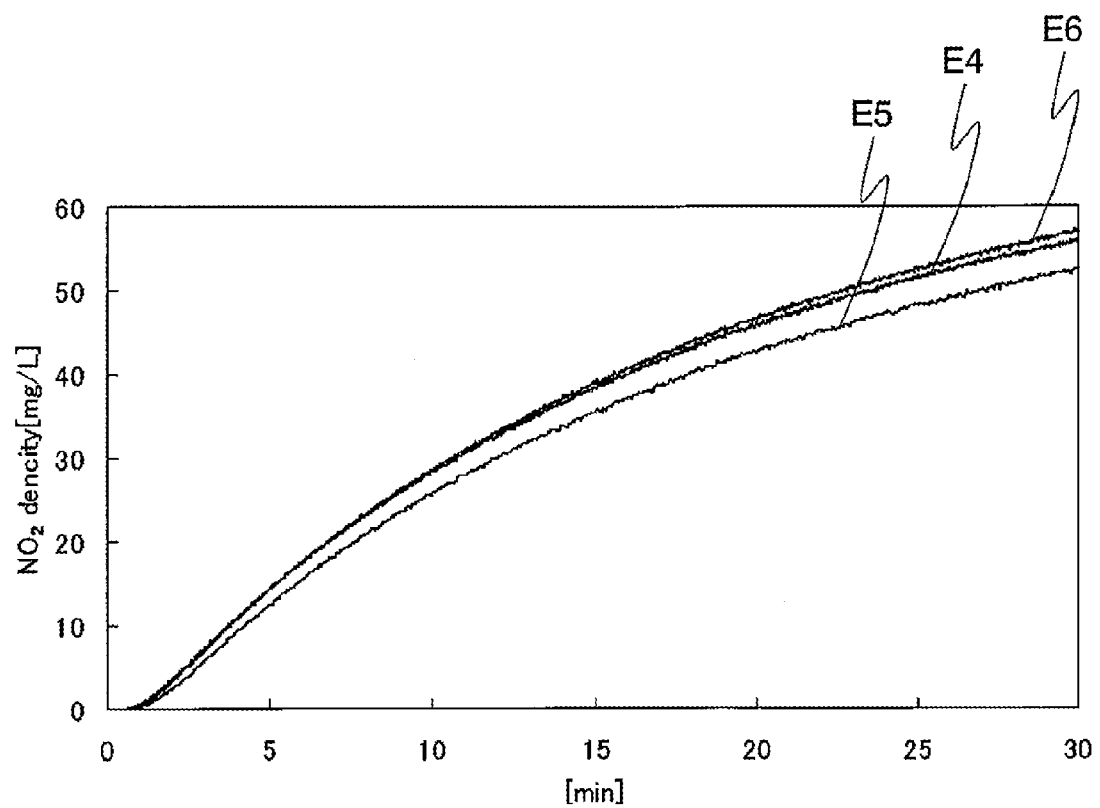
FIG. 7 is a graph illustrating the results of Examples 4 to 6.

In the circulating path shown in FIG. 6, when the internal pressure of the chamber 1 was vacuum (−101 kPa (relative pressure)), the air (dew point −60° C.) was filled such that the internal pressure of the chamber 1 was to be −5 kPa (relative pressure). The air was made to circulate by the pressure device 61 and pressure device 62, and the flow resistive portion 51, flow resistive portion 52, and flow resistive portion 53 were adjusted such that the internal pressure of the plasma generator 2 was to be from 60 to 70 kPa (absolute pressure), and the flow volume of the gas was to be 8 LPM±1 LPM. Two electrodes were respectively inserted to the plasma generator 21 and plasma generator 22, and electric power applied to the plasma generator 21 and plasma generator 22 was 160 W, respectively. The concentration of the high concentration $NO_2$ gas was measured over time by the $NO_2$ concentration measuring means 7. The result is shown in FIG. 7. The reference numeral E4 is a graph showing the changes of the concentration of the high concentration $NO_2$ gas per electrode over time according to Example 4.

Example 5

Other than that the flow resistive portion 51, flow resistive portion 52, and flow resistive portion 53 were adjusted to obtain the flow volume of the gas of 5 LPM±1 LPM, the arrangement was the same as that of Example 4. The concentration of the high concentration $NO_2$ gas was measured over time. The result is shown in FIG. 7. The reference numeral E5 is a graph showing the changes of the concentration of the high concentration $NO_2$ gas per electrode over time according to Example 5.

Example 6

Other than that the flow resistive portion 51, flow resistive portion 52, and flow resistive portion 53 were adjusted to obtain the flow volume of the gas of 12 LPM±1 LPM, and a pressure device 63 and pressure device 64 were used together, the arrangement was the same as that of Example 4. The concentration of the high concentration $NO_2$ gas was measured over time. The result is shown in FIG. 7. The reference numeral E6 is a graph showing the changes of the concentration of the high concentration $NO_2$ gas per electrode over time according to Example 6.

From Examples 4 to 6, it was found that the generation speed of the high concentration $NO_2$ gas is the same level in the case the flow volume of the gas is 8 LPM or above, and the difference was little even when the flow volume is 5 LPM.

(The Concentration of High Concentration $NO_2$ Gas in the Case NOx Gas Mixture is Not Circulated in the Circulating Path)

Comparative Example 1

Figure 8:
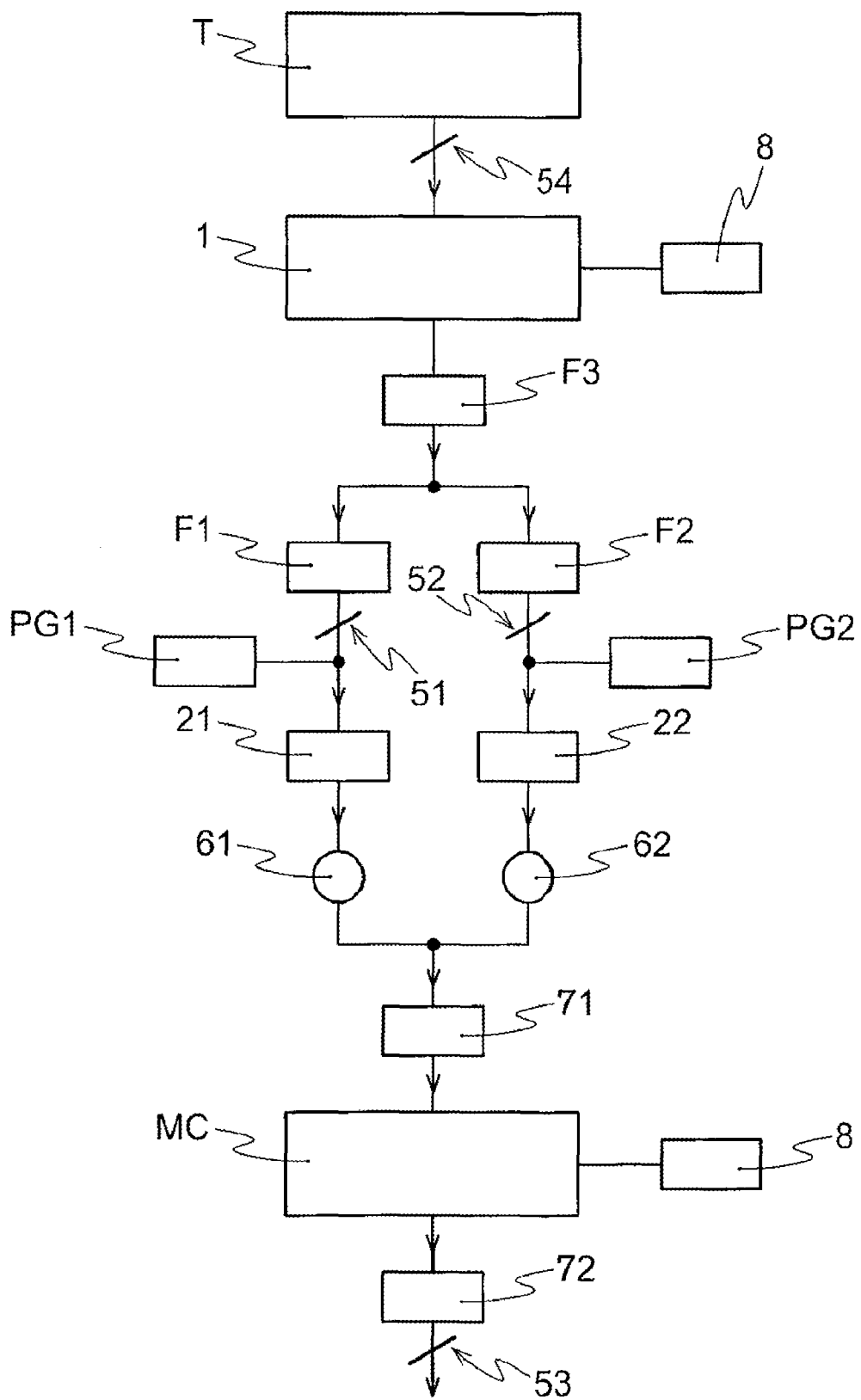
FIG. 8 is an explanatory view illustrating a circulating path used in an Embodiment (Comparative Examples 1 and 2) of the present invention.
Figure 9:
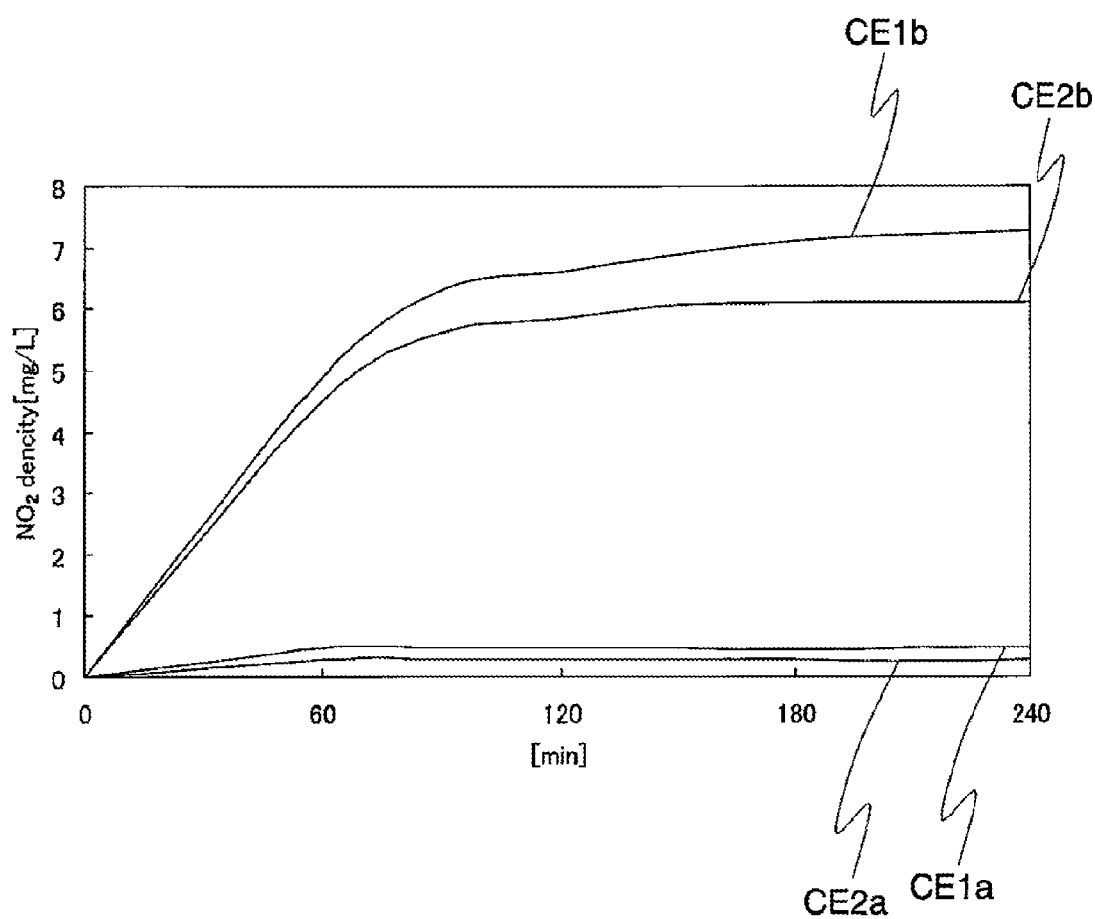
FIG. 9 is a graph illustrating the results of Comparative Examples 1 and 2.

In the circulating path shown in FIG. 8, when the internal pressure of the chamber 1 was vacuum (−101 kPa (relative pressure)), the air (dew point −60° C.) was filled such that the internal pressure of the chamber 1 was to be −5 kPa (relative pressure). The pressure device 61 and pressure device 62 were actuated, and the flow resistive portion 53 was released. The flow resistive portion 51, flow resistive portion 52, flow resistive portion 54, and the flow meter F1 were adjusted such that the internal pressures of the plasma generators 21 and 22 were to be from 60 to 70 kPa (absolute pressure), the flow volume was to be 16 LPM±1 LPM (8 LPM per electrode), and the internal pressure of the chamber 1 was to be −5 kPa (relative pressure). The pressure device 61 and pressure device 62 were stopped, and the flow resistive portion 53 was closed such that a middle chamber MC was made to be vacuumed (−95 kPa (relative pressure)). After adjusting the flow volume in the plasma generator 2 to be 5 LPM by actuating the pressure device 61 and pressure device 62, the plasma was ignited. The concentration of the high concentration $NO_2$ gas was measured by an $NO_2$ concentration measuring means 71 and $NO_2$ concentration measuring means 72. The number of electrodes was four, and 160 W of electric power was applied. The result is shown in FIG. 9. The reference numeral CE1a is a graph showing the changes of the concentration of the high concentration $NO_2$ gas per electrode over time immediately after the plasma according to Comparative Example 1. The reference numeral CE1b is a graph showing the changes of the concentration of the high concentration $NO_2$ gas per electrode over time immediately after the middle chamber MC according to Comparative Example 1. The reference numeral T is a dry air storage tank, and the reference numeral F3 is an automatic flow volume adjusting mechanism.

Comparative Example 2

Other than that after vacuuming the middle chamber MC, the flow volume in the plasma generator 2 was adjusted to be 8 LPM by actuating the pressure device 61 and pressure device 62, the arrangement was the same as that of Comparative Example 1. The concentration of the high concentration $NO_2$ gas was measured. The result is shown in FIG. 9. The reference numeral CE2a is a graph showing the changes of the concentration of the high concentration $NO_2$ gas per electrode over time immediately after the plasma according to Comparative Example 2. The reference numeral CE2b is a graph showing the changes of the concentration of the high concentration $NO_2$ gas per electrode over time immediately after the middle chamber MC according to Comparative Example 2.

From FIG. 9, it was found that the concentration of $NO_2$ does not increase and is at most 7 mg/L (36.50 ppm when the unit is converted to ppm), and it was found the $NO_2$ gas can be enhanced by circulation.

Lightning Stability of Plasma by Internal Pressure of Plasma Generating Portion

Example 7

Figure 10:
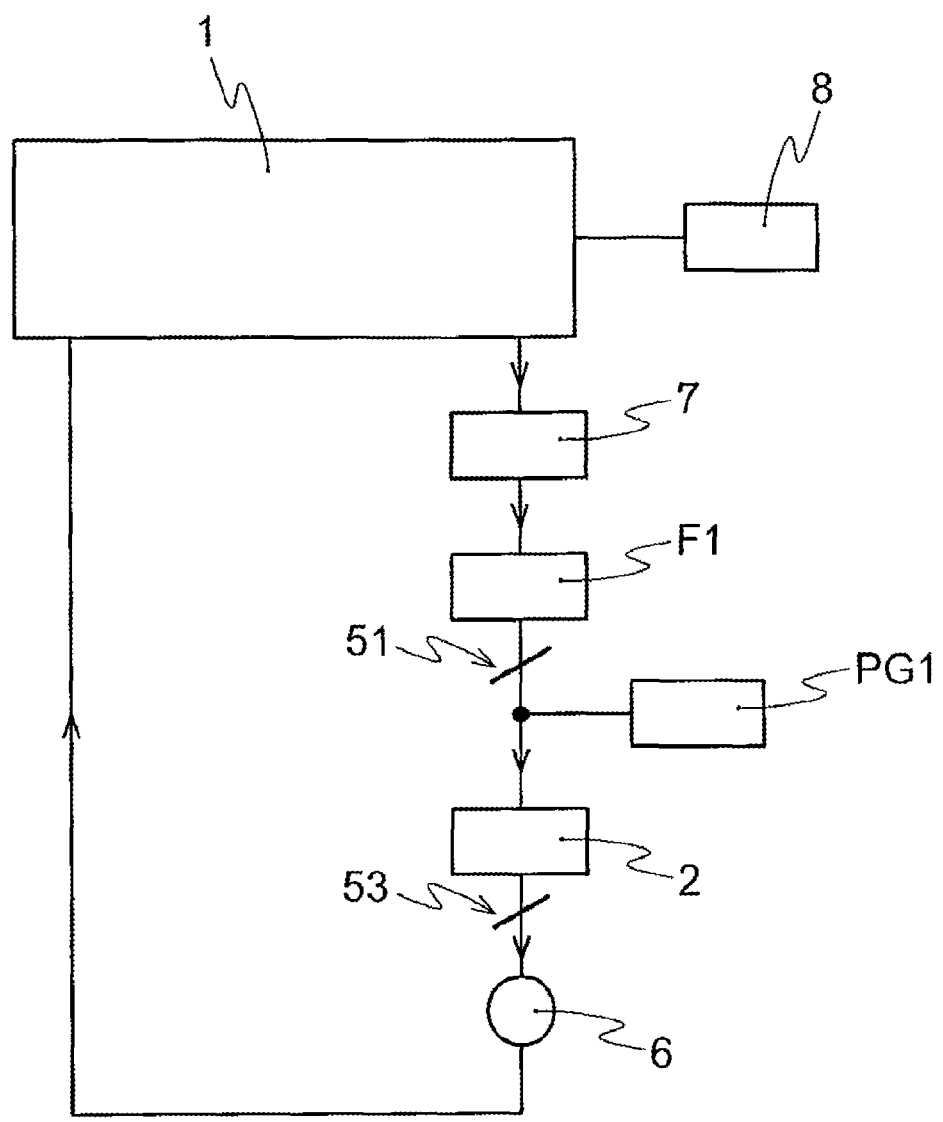
FIG. 10 is an explanatory view illustrating a circulating path used in an Embodiment (Examples 7 to 13 and Comparative Example 3) of the present invention.

In the circulating path shown in FIG. 10, when the internal pressure of the chamber 1 was vacuum (−101 kPa (relative pressure)), the air (dew point −60° C.) was filled such that the internal pressure of the chamber 1 was to be −5 kPa (relative pressure). The internal pressure of the plasma generator 2 was made to be −20 kPa (relative pressure) by actuating the pressure device 6, and the flow resistive portion 51, flow resistive portion 53, and flow meter F1 were adjusted such that the flow volume in the plasma generator 2 was to be 16 LPM±1 LPM (8 LPM per electrode). The number of electrode was two, and 120 of electric power was applied. The plasma lightning time was 1 hour. The test was performed three times, and an average was calculated. The result is shown in Table 1.

Comparative Example 3

Figure 11:
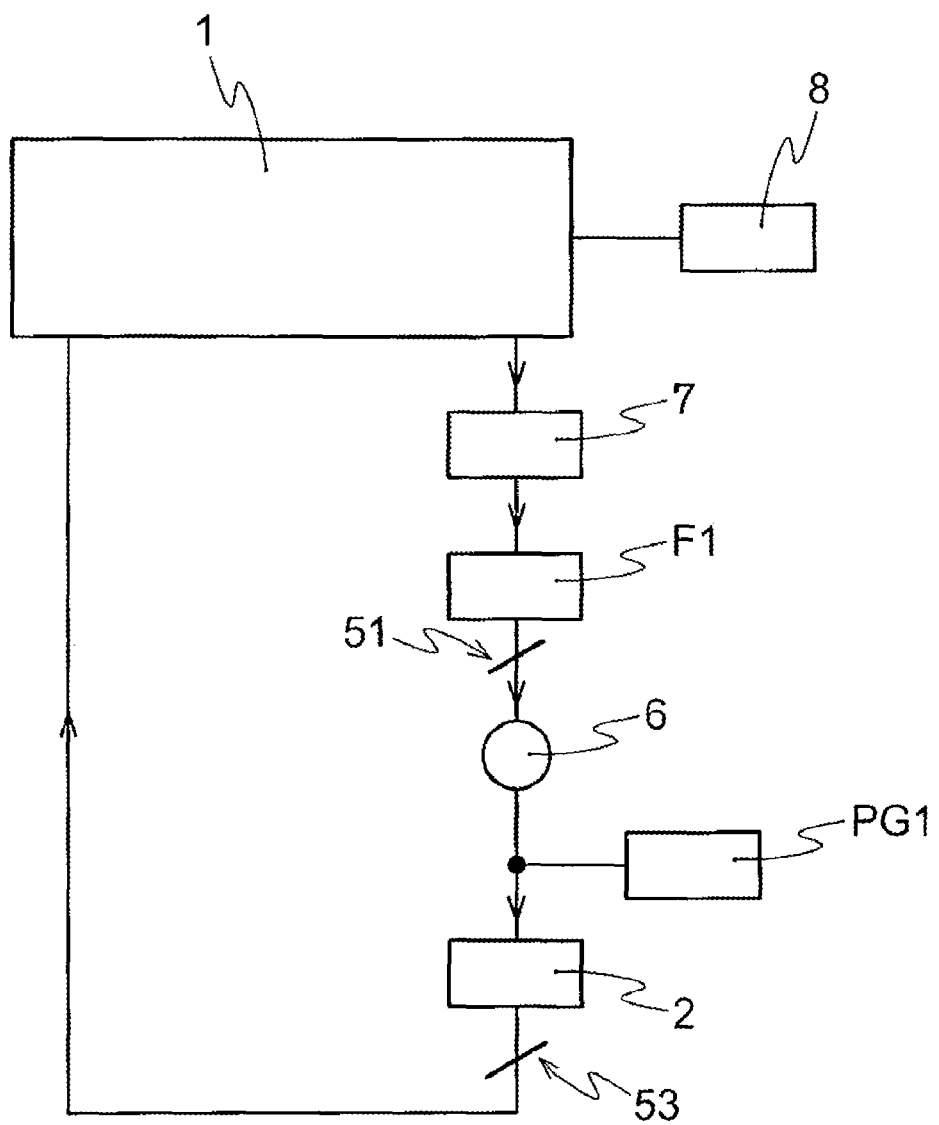
FIG. 11 is an explanatory view illustrating a circulating path used in an Embodiment (Comparative Examples 5 to 7) of the present invention.

In the circulating path shown in FIG. 11, when the internal pressure of the chamber 1 was vacuum (−101 kPa (relative pressure)), the air (dew point −60° C.) was filled such that the internal pressure of the chamber 1 was to be −5 kPa (relative pressure). The internal pressure of the plasma generator 2 was made to be 0 kPa (relative pressure) by actuating the pressure device 6, and the flow resistive portion 51, flow resistive portion 52, and flow meter F1 were adjusted such that the flow volume in the plasma generator 2 was to be 16 LPM±1 LPM (8 LPM per electrode). The number of electrode was four, and 160 W of electric power was applied. The plasma lightning time was 1 hour. The test was performed three times, and an average was calculated. The result is shown in Table 1.

Comparative Example 4

In the circulating path shown in FIG. 11, when the internal pressure of the chamber 1 was vacuum (−101 kPa (relative pressure)), the air (dew point −60° C.) was filled such that the internal pressure of the chamber 1 was to be −5 kPa (relative pressure). The internal pressure of the plasma generator 2 was made to be −20 kPa (relative pressure) by actuating the pressure device 6, and the flow resistive portion 51, flow resistive portion 52, and flow meter F1 were adjusted such that the flow volume in the plasma generator 2 was to be 16 LPM±1 LPM (8 LPM per electrode). The number of electrode was four, and 160 W of electric power was applied. The plasma lightning time was 1 hour. The test was performed three times, and an average was calculated. The result is shown in Table 1.

TABLE 1

| | Internal pressure of plasma generating portion 2 [kPa] | Concentration of high concentration $NO_2$ gas [mg/L] | | | |
|---|---|---|---|---|---|
| | | Test 1 | Test 2 | Test 3 | Average |
| Example 7 | −20 | 70 | 70 | 70 | 70 |
| Comparative Example 3 | 0 | 28 | 52.7 | 40.1 | 40.3 |
| Comparative Example 4 | 20 | 13.3 | 47.1 | 20.9 | 27.1 |

As shown in Table 1, the concentration of the high concentration $NO_2$ gas increased to 70 mg/L, and the plasma did not turn off in Example 7. On the other hand, the plasma turned off during the plasma lightening time (1 hour) in Comparative Example 3 and Comparative Example 4, and the concentration of the high concentration $NO_2$ gas increased only to the values as shown in Table 1. Accordingly, it was found that the lightening of plasma is maintained in the case the internal pressure of the plasma generator 2 is negative, however, plasma is likely to turn off in the case the internal pressure of the plasma generator 2 is 0 or positive.

Damage on Electrode in the Case of Changing the Flow Volume of Gas

Comparative Example 5

In the circulating path shown in FIG. 4, when the internal pressure of the chamber 1 was vacuum (−101 kPa (relative pressure)), the air (dew point −60° C.) was filled such that the internal pressure of the chamber 1 was to be −5 kPa (relative pressure). The pressure device 61 and pressure device 62 were actuated, and the flow resistive portion 51 and flow resistive portion 52 were adjusted to control the flow volume of the gas such that the flow meter F1 and flow meter F2 indicated 1 LPM for generating the high concentration $NO_2$ gas. The pressure was adjusted such that the value of the pressure meter PG1 and pressure meter PG2 indicated from 60 to 70 kPa (absolute pressure). The number of electrodes was four, and 160 W of electric power was applied. The plasma lightening time was 1 hour. As a result, two electrodes out of four were damaged.

Comparative Example 6

Other than adjusting the flow meter F1, flow meter F2, flow resistive portion 51, and flow resistive portion 52 such that the flow volume of the gas was to be 2 LPM, the high concentration $NO_2$ gas was generated in the same manner as in Comparative Example 5. As a result, one electrode out of four was damaged.

From the result of Comparative Example 5 and Comparative Example 6, it was found that the electrode body is not sufficiently cooled by a gas flow in the case a gas flow is 5 LPM or less, and the alumina coat provided on the surface of the electrode made of titanium is damaged as a result.
(Concentration of High Concentration $NO_2$ Gas in the Case of Changing Ratio of Oxygen in Ingredient Gas)

Example 8

Figure 12:
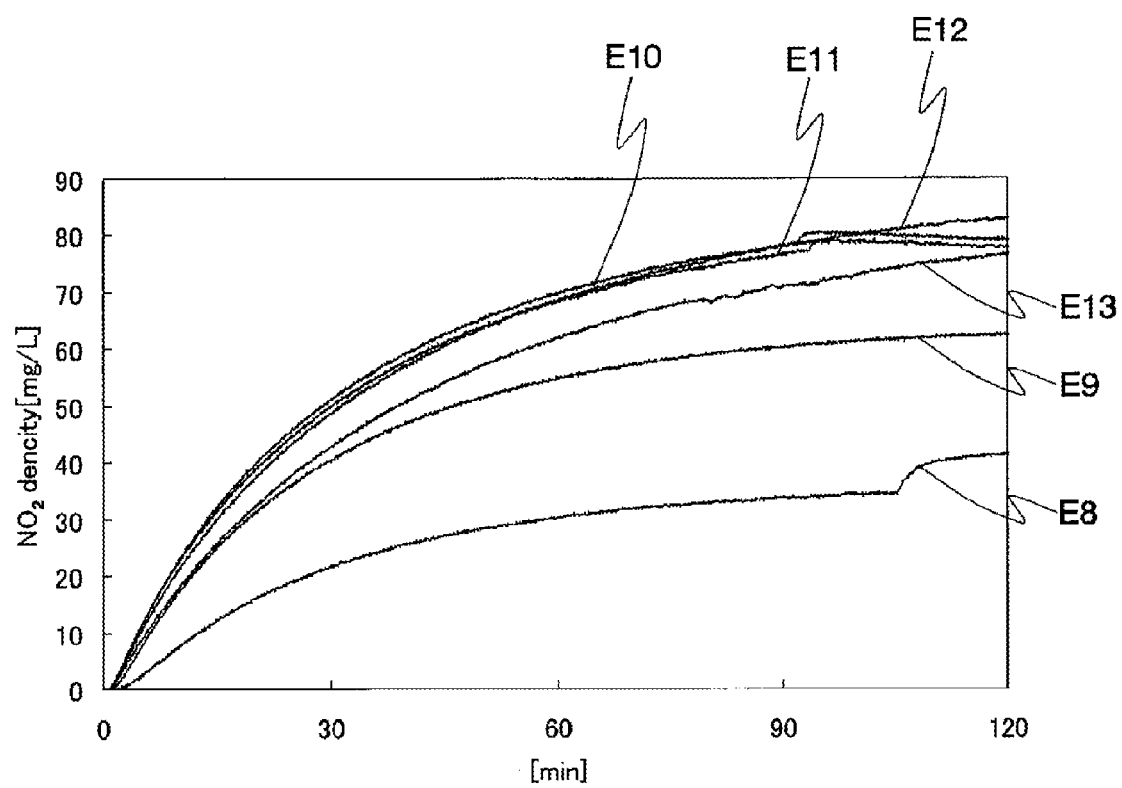
FIG. 12 is a graph illustrating the results of Examples 8 to 13.

In the circulating path shown in FIG. 10, when the internal pressure of the chamber 1 was vacuum (−101 kPa (relative pressure)), an ingredient gas (10% oxygen, 90% nitrogen) was filled such that the internal pressure of the chamber 1 was to be −5 kPa (relative pressure). The flow volume of the gas was adjusted to be 16 LPM by actuating the circulating pressure device 6 to generate the high concentration $NO_2$ gas. The concentration thereof was measured by the $NO_2$ concentration measurement means 7. The pressure was adjusted such that the value of the pressure meter PG1 indicated from 60 to 70 kPa (absolute pressure). The number of electrodes was two, and 120 W of electric power was applied. The result is shown in FIG. 12. The reference numeral E8 is a graph showing the concentration of the high concentration $NO_2$ gas over time according to Example 8.

Example 9

Other than that an ingredient gas (20% oxygen, 80% nitrogen) was used, the high concentration $NO_2$ gas was generated in the same manner as in Example 8. The result is shown in FIG. 12. The reference numeral E9 is a graph showing the concentration of the high concentration $NO_2$ gas over time according to Example 9.

Example 10

Other than that an ingredient gas (40% oxygen, 60% nitrogen) was used, the high concentration $NO_2$ gas was generated in the same manner as in Example 8. The result is shown in FIG. 12. The reference numeral E10 is a graph showing the concentration of the high concentration $NO_2$ gas over time according to Example 10.

Example 11

Other than that an ingredient gas (50% oxygen, 50% nitrogen) was used, the high concentration $NO_2$ gas was generated in the same manner as in Example 8. The result is shown in FIG. 12. The reference numeral E11 is a graph showing the concentration of the high concentration $NO_2$ gas over time according to Example 11.

Example 12

Other than that an ingredient gas (60% oxygen, 40% nitrogen) was used, the high concentration $NO_2$ gas was generated in the same manner as in Example 8. The result is shown in FIG. 12. The reference numeral E12 is a graph showing the concentration of the high concentration $NO_2$ gas over time according to Example 12.

Example 13

Other than that an ingredient gas (80% oxygen, 20% nitrogen) was used, the high concentration $NO_2$ gas was generated in the same manner as in Example 8. The result is shown in FIG. 12. The reference numeral E13 is a graph showing the concentration of the high concentration $NO_2$ gas over time according to Example 13.

As shown in FIG. 12, the concentration of the high concentration $NO_2$ gas increased to approximately 35 (mg/L) in the case of using the ingredient gas (oxygen 10%, nitrogen 90%) of Example 8, the concentration of the high concentration $NO_2$ gas increased to approximately 62 (mg/L) in the case of using the ingredient gas (oxygen 20%, nitrogen 80%) of Example 9, and the concentration of the high concentration $NO_2$ gas increased to the maximum of approximately 80 (mg/L) in the case of using the ingredient gas (oxygen 80%, nitrogen 20%) of Example 13. The concentration of the high concentration $NO_2$ gas increased above the maximum of approximately 86 (mg/L) in the case of using the ingredient gas (oxygen 40%, nitrogen 60%) of Example 10, the ingredient gas (oxygen 50%, nitrogen 50%) of Example 11, and the ingredient gas (oxygen 60%, nitrogen 40%) of Example 12. In addition, it was found that the increasing speed is also fast.

The concentration of the high concentration $NO_2$ gas generated in Example 12 is approximately 86 mg/L, and it is 44,900 ppm when the unit is converted to ppm. In addition, since $NO_2$ and $N_2O_4$ are present under an equilibrium state in the high concentration $NO_2$ gas, 85,800 ppm of $NO_2$ is theoretically present in practical. To further increase the concentration of $NO_2$, it is achievable by increasing the electric power of the plasma generator 2. According to the present invention, the concentration of $NO_2$ can therefore be increased to approximately 100,000 ppm.

Example 14

Figure 13:
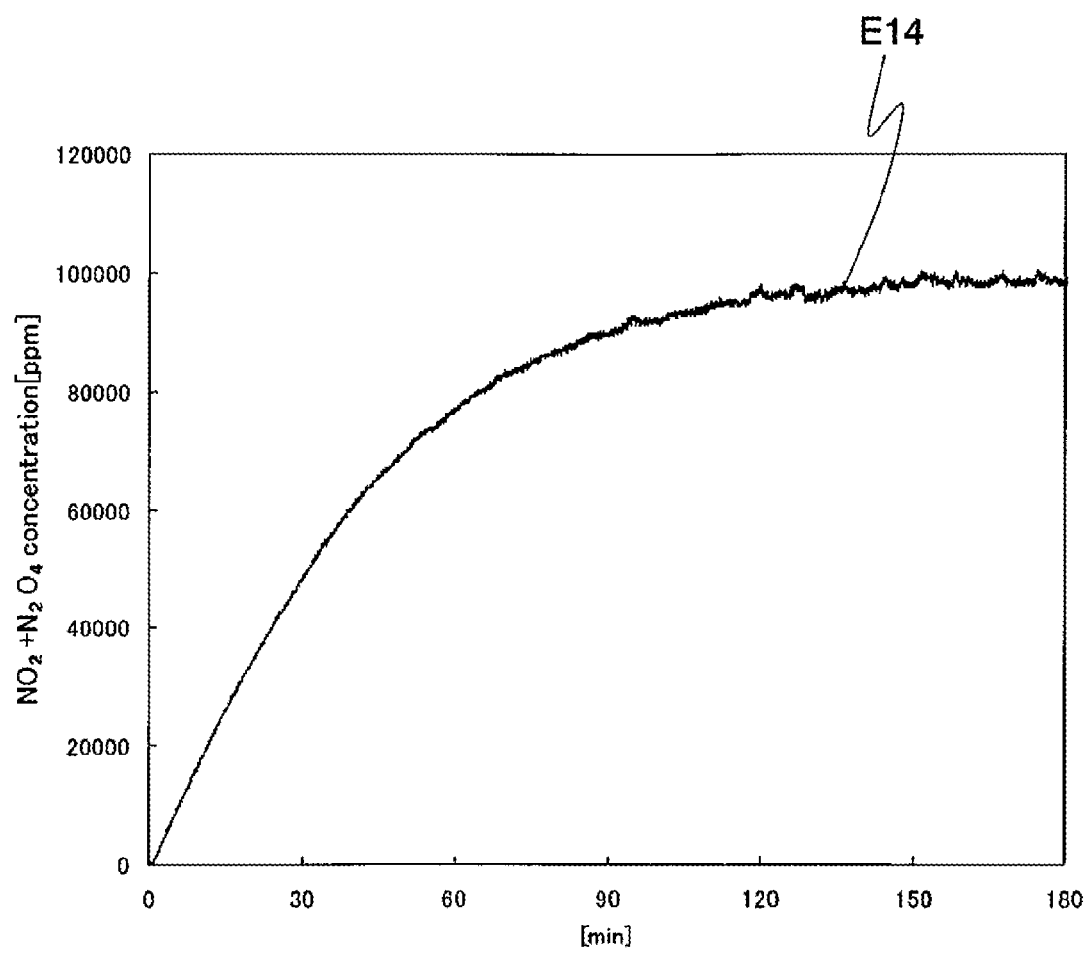
FIG. 13 is a graph illustrating the results of Example 14.

Other than that 160 W of electric power was applied to the plasma generator and the plasma lightning time was extended, the high concentration $NO_2$ gas was generated in the same manner as in Example 11. The result is shown in FIG. 13. The reference numeral E14 is a graph showing the concentration of the high concentration $NO_2$ gas over time according to Example 14. As shown in FIG. 13, the total amount of $NO_2$ and $N_2O_4$ present under an equilibrium state was approximately 100,000 ppm.

INDUSTRIAL APPLICABILITY

According to the high concentration $NO_2$ generating system of the present invention and the method for generating high concentration $NO_2$ using the generating system, $NO_2$ can be simply and selectively concentrated (approximately 500 ppm or above). In addition, since a gas mixture including nitrogen and oxygen is used as an ingredient, the management of ingredients is simple and highly safe, and the high concentration of $NO_2$ can be simply and selectively prepared on demand.

EXPLANATION OF SYMBOLS 1 chamber
1a inlet portion
1b exhaust pump
1c inlet pipe
1d, 1g, V1 closure means
1e gas drying means
1f exhaust pipe
1h exhaust pump
2 plasma generator
2a microwave generating apparatus
2b waveguide
2c plasma generating portion
2d conducting shaft
2e conducting tube
2f antenna portion
2g center electrode
2h shielding film
2i ring-shaped space
2j pipe
2k shielding tube
3 circulating apparatus
4 circulating path
5 flow resistive portion
5a orifice
6 pressure device
7 $NO_2$ concentration measurement sensor
8 pressure detecting means
CE1a concentration of the high concentration $NO_2$ gas per electrode over time immediately after plasma according to Comparative Example 1
CE1b concentration of the high concentration $NO_2$ gas per electrode over time immediately after middle chamber according to Comparative Example 1
CE2a concentration of the high concentration $NO_2$ gas per electrode over time immediately after plasma according to Comparative Example 2
CE2b concentration of the high concentration $NO_2$ gas per electrode over time immediately after middle chamber according to Comparative Example 2
E1 concentration of high concentration $NO_2$ gas according to Example 1
E2 concentration of high concentration $NO_2$ gas according to Example 2
E3 concentration of high concentration $NO_2$ gas according to Example 3
E4 concentration of high concentration $NO_2$ gas per electrode according to Example 4
E5 concentration of high concentration $NO_2$ gas per electrode according to Example 5
E6 concentration of high concentration $NO_2$ gas per electrode according to Example 6
E8 concentration of high concentration $NO_2$ gas according to Example 8
E9 concentration of high concentration $NO_2$ gas according to Example 9
E10 concentration of high concentration $NO_2$ gas according to Example 10
E11 concentration of high concentration $NO_2$ gas according to Example 11
E12 concentration of high concentration $NO_2$ gas according to Example 12
E13 concentration of high concentration $NO_2$ gas according to Example 13
F1, F2 flow meter
F3 flow volume adjusting mechanism
f filter
T dry air storage tank
MC middle chamber
PG1, PG2 pressure device

What is claimed is:

1. A method for generating high concentration $NO_2$, comprising circulating a NOx gas mixture in a circulating path formed by a chamber, a plasma generator, and a circulating means until $NO_2$ concentration reaches 500 ppm to 100,000 ppm by using a high concentration $NO_2$ gas generating system comprising:
   the circulating path configured by connecting the chamber, the plasma generator, and the circulating means;
   wherein $NO_2$ is generated by circulating the NOx gas mixture including nitrogen and oxygen in the circulating path.

2. The method for generating high concentration $NO_2$ according to claim 1, wherein ambient air is employed for the gas mixture.

3. The method for generating high concentration $NO_2$ according to claim 1, wherein dry air with a dew point from 0 to $-90°$ C. is used for the gas mixture.

4. The method for generating high concentration $NO_2$ according to claim 1, wherein an internal pressure of a plasma generating portion of said plasma generator is from 20 to 90 kPa (absolute pressure).

5. The method for generating high concentration $NO_2$ according to claim 1, wherein a pressure difference between atmospheric pressure and an internal pressure of an interval from a pressure device through said chamber connected to said pressure device at a downstream side of a path to a flow resistive portion connected to said chamber at said downstream side of said path is set between approximately $-1$ and $-50$ kPa (relative pressure).

6. The method for generating high concentration $NO_2$ according to claim 1, wherein an internal pressure of an interval from a pressure device through said chamber connected to said pressure device at a downstream side of a path to a flow resistive portion connected to said chamber at said downstream side of said path is maintained to be a positive pressure relative to atmospheric pressure.

7. The method for generating high concentration $NO_2$ according to claim 1, wherein a flow volume of said NOx gas mixture circulating in said circulating path is 5 LPM or above.

* * * * *